（12） United States Patent
Jaworski et al.

(10) Patent No.: US 10,328,174 B2
(45) Date of Patent: Jun. 25, 2019

(54) PORTABLE MICROORGANISM SANITATION SYSTEM

(71) Applicant: Radiant Industrial Solutions, LLC, Houston, TX (US)

(72) Inventors: Drew Jaworski, Houston, TX (US); Troy Smith, Houston, TX (US)

(73) Assignee: RADIANT INDUSTRIAL SOLUTIONS, LLC, Houston, TX (US)

( * ) Notice: Subject to any disclaimer, the term of this patent is extended or adjusted under 35 U.S.C. 154(b) by 0 days.

(21) Appl. No.: 16/119,023

(22) Filed: Aug. 31, 2018

(65) Prior Publication Data

US 2019/0060505 A1 Feb. 28, 2019

Related U.S. Application Data

(60) Provisional application No. 62/552,998, filed on Aug. 31, 2017.

(51) Int. Cl.
*A61L 9/04* (2006.01)
*A61L 9/20* (2006.01)

(52) U.S. Cl.
CPC ............... *A61L 9/205* (2013.01); *A61L 9/046* (2013.01); *A61L 2209/12* (2013.01); *A61L 2209/14* (2013.01); *A61L 2209/212* (2013.01)

(58) Field of Classification Search
None
See application file for complete search history.

(56) References Cited

U.S. PATENT DOCUMENTS

| 3,418,069 | A | | 12/1968 | Decupper et al. | |
|---|---|---|---|---|---|
| 4,087,925 | A | * | 5/1978 | Bienek | A47K 10/48 250/432 R |
| 4,591,724 | A | * | 5/1986 | Fuse | B01J 19/123 250/454.11 |
| 4,896,042 | A | | 1/1990 | DiCamillo | |
| 5,144,146 | A | | 9/1992 | Wekhof | |
| 5,330,722 | A | * | 7/1994 | Pick | A61L 9/20 250/436 |
| 5,712,487 | A | * | 1/1998 | Adachi | F26B 3/28 250/492.1 |
| 5,932,886 | A | * | 8/1999 | Arai | B01J 19/123 250/492.1 |

(Continued)

*Primary Examiner* — Andrew Smyth
(74) *Attorney, Agent, or Firm* — Invention To Patent Services; Alex Hobson

(57) ABSTRACT

A portable microorganism sanitation system produces UV light and air treatment for treating an enclosed space, such as a room. A portable microorganism sanitation system incorporates a plurality of UV light sources configured around a lamp tower having reflective surfaces to produce emitted UV and reflected UV light in a wide range of angles. This wide range of angles of the emitted and reflected UV light enables more complete and direct impingement of UV light on surfaces in the enclosure or room. The portable microorganism sanitation system also incorporates active air treatment, wherein an air moving device draws airflow into a conduit inside of the lamp tower and then through airflow outlets. The airflow outlets are configured to expose the outlet airflow to the UV light sources, thereby treating the airflow to destroy microorganism therein. Photocatalyst may be configured on the surfaces of the lamp tower to promote microorganism destruction.

19 Claims, 9 Drawing Sheets

(56) References Cited

U.S. PATENT DOCUMENTS

| | | | |
|---|---|---|---|
| 5,997,812 A * | 12/1999 | Burnham | A23L 2/50 |
| | | | 210/695 |
| 6,242,753 B1 | 6/2001 | Sakurai | |
| 6,759,664 B2 | 7/2004 | Thompson et al. | |
| 6,773,584 B2 | 8/2004 | Saccomanno | |
| 6,797,966 B2 | 9/2004 | Summers et al. | |
| 7,326,387 B2 * | 2/2008 | Arts | A61L 2/10 |
| | | | 422/186.3 |
| 9,707,306 B2 | 7/2017 | Farren et al. | |
| 9,782,505 B2 | 10/2017 | Lyslo et al. | |
| 2002/0085947 A1 | 7/2002 | Deal | |
| 2003/0155531 A1 | 8/2003 | Clarke et al. | |
| 2004/0052702 A1 | 3/2004 | Calvin et al. | |
| 2006/0284109 A1 | 12/2006 | Culbert et al. | |
| 2011/0293471 A1 | 12/2011 | Hill et al. | |
| 2014/0158917 A1 * | 6/2014 | Stibich | A61L 2/10 |
| | | | 250/504 R |
| 2016/0271282 A1 * | 9/2016 | Trapani | A61L 2/202 |

* cited by examiner

| Standard 52.2 Minimum Efficiency Reporting Value | Dust Spot Efficiency | Arrestance | Typical Controlled Contaminant | Typical Applications and Limitations | Typical Air Filter/Cleaner Type |
|---|---|---|---|---|---|
| 20 | n/a | n/a | < 0.30 pm particle size | Cleanrooms | >99.999% eff. On .10-.20 pm Particles |
| 19 | n/a | n/a | Virus (unattached) | Radioactive Materials | Particles |
| 18 | n/a | n/a | Carbon Dust | Pharmaceutical Mfn. | Particulates |
| 17 | n/a | n/a | All Combustion smoke | Carcinogenic Materials | >99.97% eff. On .30 pm Particles |
| 16 | n/a | n/a | .30-1.0 pm Particle Size | General Surgery | Bag Filter - Nonsupported microfine fiberglass or synthetic media, 12-36 in. deep, 6-12 pockets |
| 15 | >95% | n/a | All Bacteria | Hospital Inpatient Care | |
| 14 | 90-95% | >98% | Most Tobacco Smoke | Smoking Lounges | |
| 13 | 89-90% | >98% | Proplet Nucli (Sneeze) | Superior Commercial Buildings | Box Filter - Rigid Style Cartridge Filters 6 to 12" deep as my use tufted or paper media. |
| 12 | 70-75% | >95% | 1.0-3.0 pm Particle Size Legionella | Superior Residential | Bag Filter - Nonsupported microfine fiberglass or synthetic media, 12-36 in. deep, 6-12 pockets |
| 11 | 60-65% | >95% | Humidifier Dust Lead Dust | Better Commercial Buildings | |
| 10 | 50-55% | >95% | Milled Flour Auto Emissions | Hospital Laboratories | Box Filter - Rigid Style Cartridge Filters 6 to 12" deep as my use tufted or paper media. |
| 9 | 40-45% | >90% | Welding Fumes | | |
| 8 | 30-35% | >90% | 3.0-10.0 pm Particle Size Mold Spores | Commercial Buildings | Pleated Filters - Disposable, extended surface area, thick with cotton-polyester blend media, cardboard frame |
| 7 | 25-30% | >90% | Hair Spray | Better Residential | |
| 6 | <20% | 85-90% | Fabric Protector Dusting Aids | Industrial Workplace | Cartridge Filters - Graded density viscous coated cube or pocket filters, synthetic media |
| 5 | <20% | 80-85% | Cement Dust Pudding Mix | Paint Booth Inlet | Throwaway - Disposable synthetic panel filter |
| 4 | <20% | 75-80% | >10.0 pm Particle Size Pollen | Minimal Filtration | Throwaway - Disposable fiberglass or synthetic panel filter |
| 3 | <20% | 70-75% | Dust Mites Sanding Dust | Residential | Washable - Aluminum Mesh |
| 2 | <20% | 65-70% | Spray Paint Dust | | |
| 1 | <20% | <65% | Textile Fibers Carpet Fibers | Window A/C Units | Electrostatic - Self charging woven panel filter |

FIG. 9

PORTABLE MICROORGANISM SANITATION SYSTEM

CROSS REFERENCE TO RELATED APPLICATIONS

This application claims the benefit of U.S., provisional patent application No. 62/552,998, filed on Aug. 31, 2017; the entirety of which is hereby incorporated by reference herein.

BACKGROUND OF THE INVENTION

Field of the Invention

This application is directed to a portable sanitation system for deactivating or killing microorganisms with ultraviolet (UV), light and treating the air within a room.

Background

There are a large number of room enclosures that require frequent cleaning to reduce the spread and proliferation of microorganism including hospital rooms, laboratories, food processing plants, elderly car facilities and high traffic area. Microorganisms may be in the air or on surfaces. Both the surfaces and air require cleaning to effectively reduce the risk of illness or infection from these microorganisms.

Ultraviolet light has been proven to effectively destroy microorganisms with an adequate exposure. However, there are many surfaces within a room that have different surface angles, and this makes a single UV light source ineffective.

Biological materials in the air, including viruses and bacteria, are an ever-increasing concern. Viruses can become airborne by coughing and sneezing, and many people are highly allergic to naturally occurring mold spores that can cause severe respiratory and other reactions. These biological contaminants move through the air, and in some cases through air handling systems, endangering the health of people gathered in tight quarters or confined spaces, such as airplanes, restaurants, and tents.

SUMMARY OF THE INVENTION

The invention is directed to a portable microorganism sanitation system for treating an enclosed space, such as a room with UV light and with active air treatment. An exemplary portable microorganism sanitation system comprises a plurality of UV light sources configured around a lamp tower having reflective surfaces to produce emitted UV and reflected UV light in a wide range of angles. This wide range of angles of the emitted and reflected UV light enables more complete and direct impingement of UV light on surfaces in the enclosure or room. The exemplary portable microorganism sanitation system also comprises active air treatment, wherein an air moving device draws airflow into a conduit inside of the lamp tower and then through airflow outlets. The airflow outlets are configured to expose the outlet airflow to the UV light sources, thereby treating the airflow to destroy microorganism therein. An exemplary A portable microorganism sanitation system is configured on a portable frame having wheel to allow the unit to be moved from room to room for sanitizing the rooms as required.

An exemplary lamp tower has reflective panels at offset angles to produce reflective cells. The offset angle of a reflective panel is the angles of the panel from a line normal to a radial line extending from a center of the lamp tower. An offset angle may be about 10 degrees or more, or about 15 degrees or more, about 25 degrees or more, about 40 degrees or more, about 60 degrees or more and any range between and including the offset angles provided. The offset angle should not be too large, or the light may be reflected back into the opposing reflective panel and may not provide enough reflected light from the portable microorganism sanitation system. A first reflective panel and second reflective panel form an intersection and the UV light source may be aligned with this intersection, or centered between a first and second reflective panel. A reflective cell comprises a UV light source configured between a first and second reflective panel. An exemplary portable microorganism sanitation system may have four or more reflective cells, six or more reflective cells, eight or more reflective cells, twelve or more reflective cells, sixteen or ore or more reflective cells and any number of reflective cells between and including the numbers provided. At least four to six reflective cells may be required to provide adequate light projection to provide direct impingement of light onto surfaces within a room or enclosure. A reflective panel may have a reflective surface, such as a mirror and may comprise a photocatalyst to aid in the destruction of microorganisms in the airflow as it passes out of airflow outlets.

An exemplary portable microorganism sanitation system comprises an airflow treatment system that comprises an air moving device, such as a fan or blower that forces air into a conduit within the lamp tower. The lamp tower itself could be the airflow conduit or a separate internal conduit may be configured within the lamp tower. In an exemplary embodiment, airflow flows into the airflow conduit from the base or top of the lamp tower and flows along the length of the lamp tower and then out through airflow outlets configured in the lamp tower, such as along the length of the lamp tower. In an exemplary embodiment, airflow enters from the base of the microorganism sanitation system and then flows up along the airflow conduit before being expelled through airflow outlets configured within the reflective cells, such as along the intersection of the first and second reflective panels. The outlet airflow will therefore flow around to the UV light sources which will increase the likelihood of any microorganisms being destroyed. The airflow outlets may be slots configured along the intersection of the reflective panels and the size of the airflow outlets may vary, along the height or length of the lamp tower. In an exemplary embodiment, the airflow from the top of the lamp tower is greater than the airflow at the base, thereby preventing too much expelled airflow from being entrained in the airflow entering the airflow conduit.

An exemplary airflow treatment system may further comprise an air filter configured to filter out particles from the air and this filter may be configured at or near the airflow inlet to the portable microorganism sanitation system such as in the base. An air filter may comprise a particle filtration media and it may be pleated to reduce pressure drop through the filter, wherein the filtration area is increase by the pleats. A filter or filters may be used to remove contaminates from the incoming airflow into the portable microorganism sanitation system. The filters may be HEPA or ULPA. An air filter or air filtration system may be configured to be HEPA efficient, thereby removing 99.7% of 0.3 μm or larger particles, or ULPA efficient removing 99.999% of 0.1 μm or larger particles from the inlet air flow. In an exemplary embodiment, the air filter removes, at least 99.95% of 0.3 μm or larger particles from the inlet air. An air filter may be defined by a MERV rating. MERV ratings are the air filtration industry's standard for measuring and reporting the efficiency of air filter, A MERV rating the filter's Minimum Efficiency Reporting Value. Because removing particles from the air is the primary function of an air filter, the MERV rating indicates the measured ability of that filter to trap particles that range in size from 3-10 microns. Most filters have a filtration rating, such as a MERV rating. A complete table of MERV ratings is provided in FIG. 9. Note that an air filter used in the portable microorganism sanitation system may have a MERV rating of about 5 or more and preferably about 8 or more, and in some cases, such as in hospital rooms, and especially operating rooms, 14 or more, wherein bacteria is filter out of the air.

Furthermore, an exemplary air treatment system, of a portable microorganism sanitation system may comprise an ozone generator, to further destroy organisms and sterilize the air. An ozone generator, such as a corona element may be configured within the airflow conduit and produce ozone gas that flows with the air through the system.

An exemplary air moving device may be sized to provide a high number of room air exchanges within a certain time period. For example, the airflow produced by an exemplary air moving device may be about 100 cubic feet per minute (CFM) or more, about 100 CFM or more, about 250 CFM or more, about 500 CFM or more, about 1000 CFM or more and any range between and including the airflow values provided.

An exemplary UV light source may be a UV lamp and the wattage may be selected based on the size of rooms or enclosures the unit is being used for. A UV lamp may have an output wattage of about 50 watts or more, about 100 watts or more, about 250 watts or more about 500 watts or more, and any range between and including the output watts provided. The total output of UV light from the portable microorganism sanitation system may be about 2,000 watts or more, about 3,000 watts or more, about 5,000 watts or more, and any range between and including the total output watts provided. The total UV light output will depend on the number of reflective cells and number of UV lamps, or light source.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEW OF THE DRAWINGS

The accompanying drawings are included to provide a further understanding of the invention and are incorporated in and constitute a part of this specification, illustrate embodiments of the invention, and together with the description serve to explain the principles of the invention.

FIG. 9 shows a table of MERV ratings for air filters.

Figure 1:
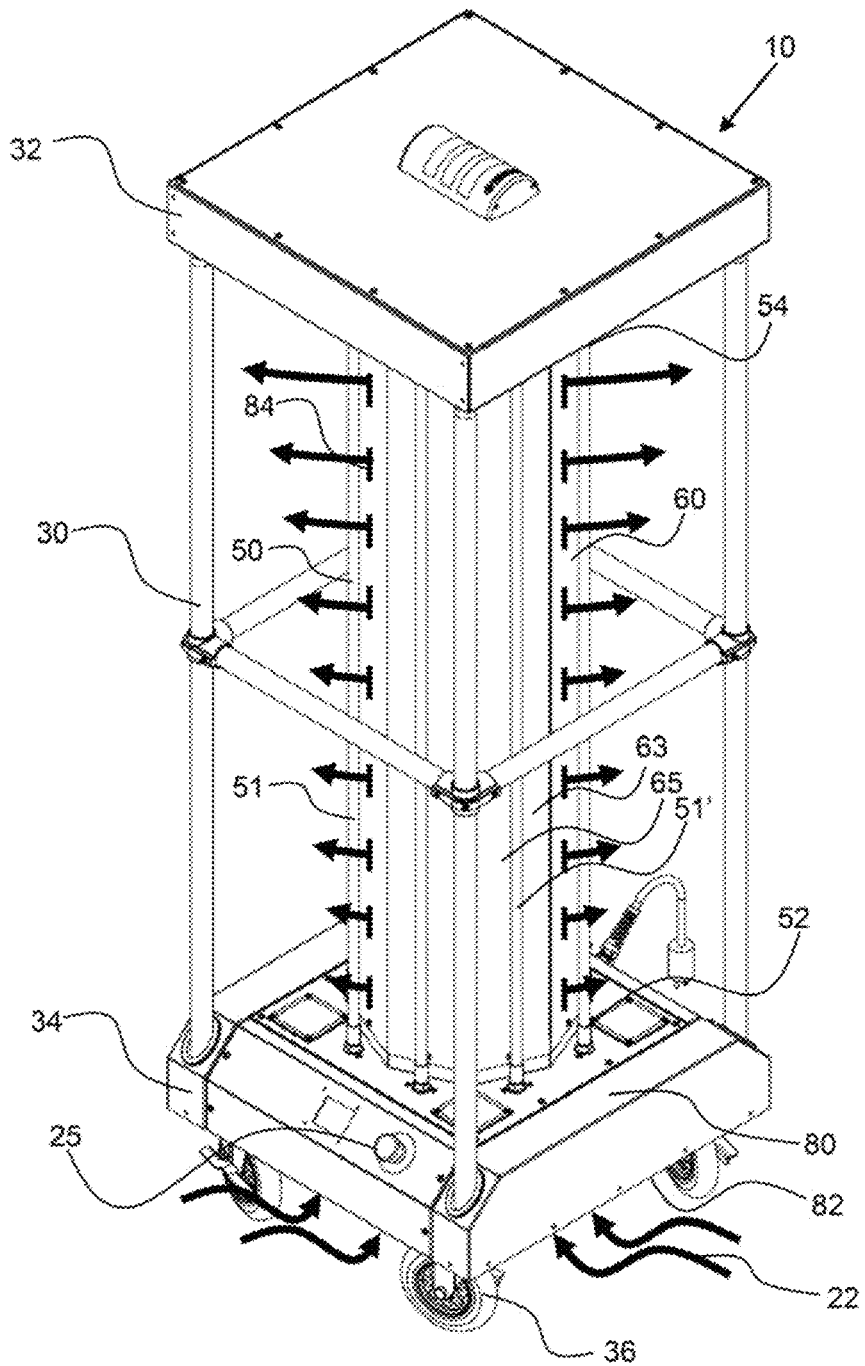
FIG. 1 shows a perspective view of an exemplary portable microorganism sanitation system having a plurality of UV light sources, such as elongated UV lamps, configured around a lamp tower having reflective panels and an air moving device the that draws air into the unit from the base and forces sanitized air out from air outlets configured along the lamp tower.
Figure 2:
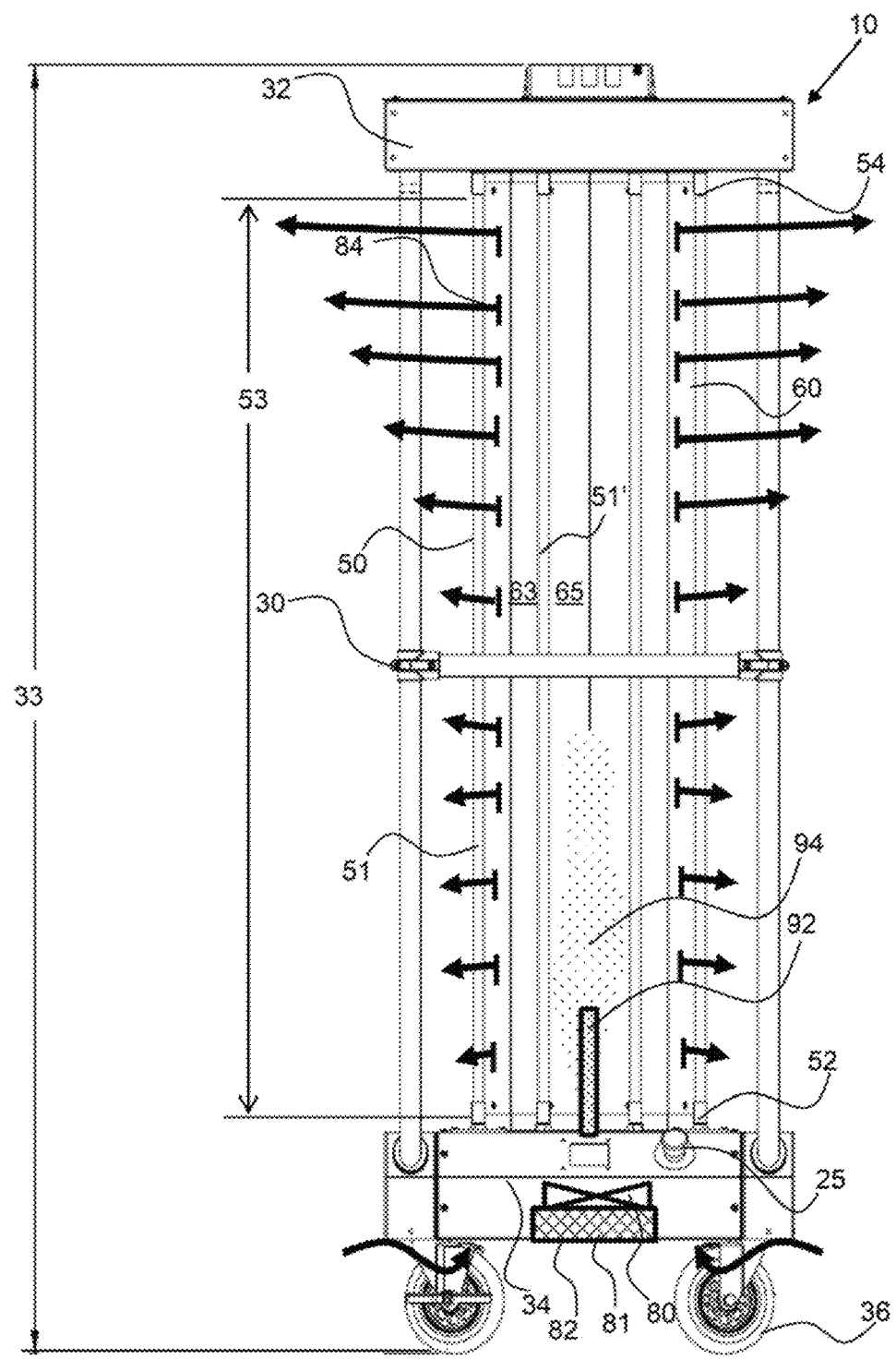
FIG. 2 shows a front view of the exemplary portable microorganism sanitation system shown in FIG. 1.
Figure 3:
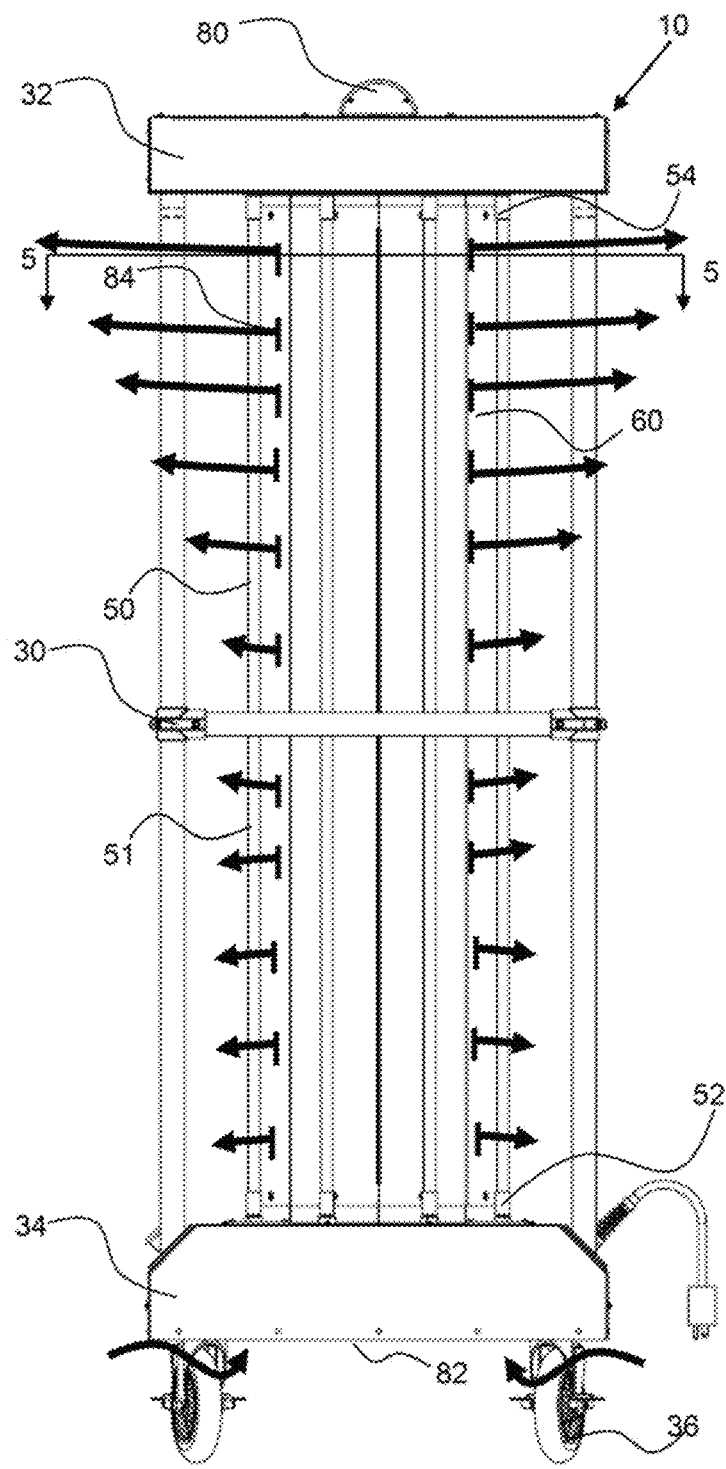
FIG. 3 shows a side view of the exemplary portable microorganism sanitation system shown in FIG. 1.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising", "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Definitions

The term destroys, as used herein, includes deactivating and/or destroying or killing microorganisms such that they are no longer active and/or alive.

Figure 4:
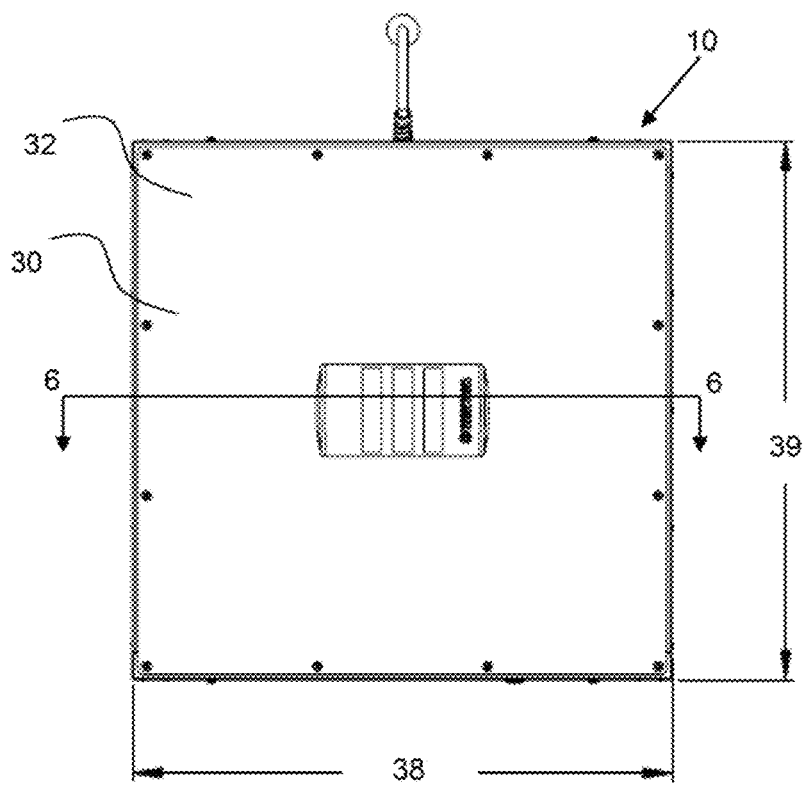
FIG. 4 shows a top view of the exemplary portable microorganism sanitation system shown in FIG. 1.

Referring to FIG. 1 to 4, an exemplary portable microorganism sanitation system 10 has a plurality of UV light sources 50, such as elongated UV lamps 51, configured around a lamp tower 60 having reflective panels 63, 65 configured to reflect light from the UV lamps 51. The UV lamps extend a length 53 from a bottom end 52 to a top end 54. The eight UV lamps are configured around the perimeter of the lamp tower and the reflective panels reflect the UV light in a plurality of reflected angles to ensure effective exposure to surfaces to be sanitized. The exemplar portable microorganism sanitation system 10 is configured on a portable frame 30, having a height 33 from the top 32 to the floor, or the bottom of the wheels 36. The controller 25 is configured in the base 34 along with an air-moving device 80, such as a fan or blower. Air is drawn into the exemplary portable microorganism sanitation system 10 through an air inlet 82 in the base 34 and is expelled out of air outlets 84 configured in the lamp tower 60. A plurality of air outlet slots 85 are configured along the length of the air tower and in an exemplary embodiment are configured between the first reflective panel 63 and second reflective panel 65. The flow or air out of the exemplary portable microorganism sanitation system may be configured to be greater at the top than at the bottom to ensure better air exchange and mixing in the room. The interior of the lamp tower may have a UV light source and the interior wall or panel surfaces may comprise a photocatalyst that kill or deactivates microorganisms. The exemplary portable microorganism sanitation system 10 can be rolled into a room and turned on to sanitize the room through UV light exposure of surfaces and through active air treatment. As shown in FIG. 4, the portable frame has a width 38 and depth 39 and the width and depth may be less than a doorway opening, such as less than about 36 inches, less than about 32 inches, or less than about 24 inches.

Figure 5:
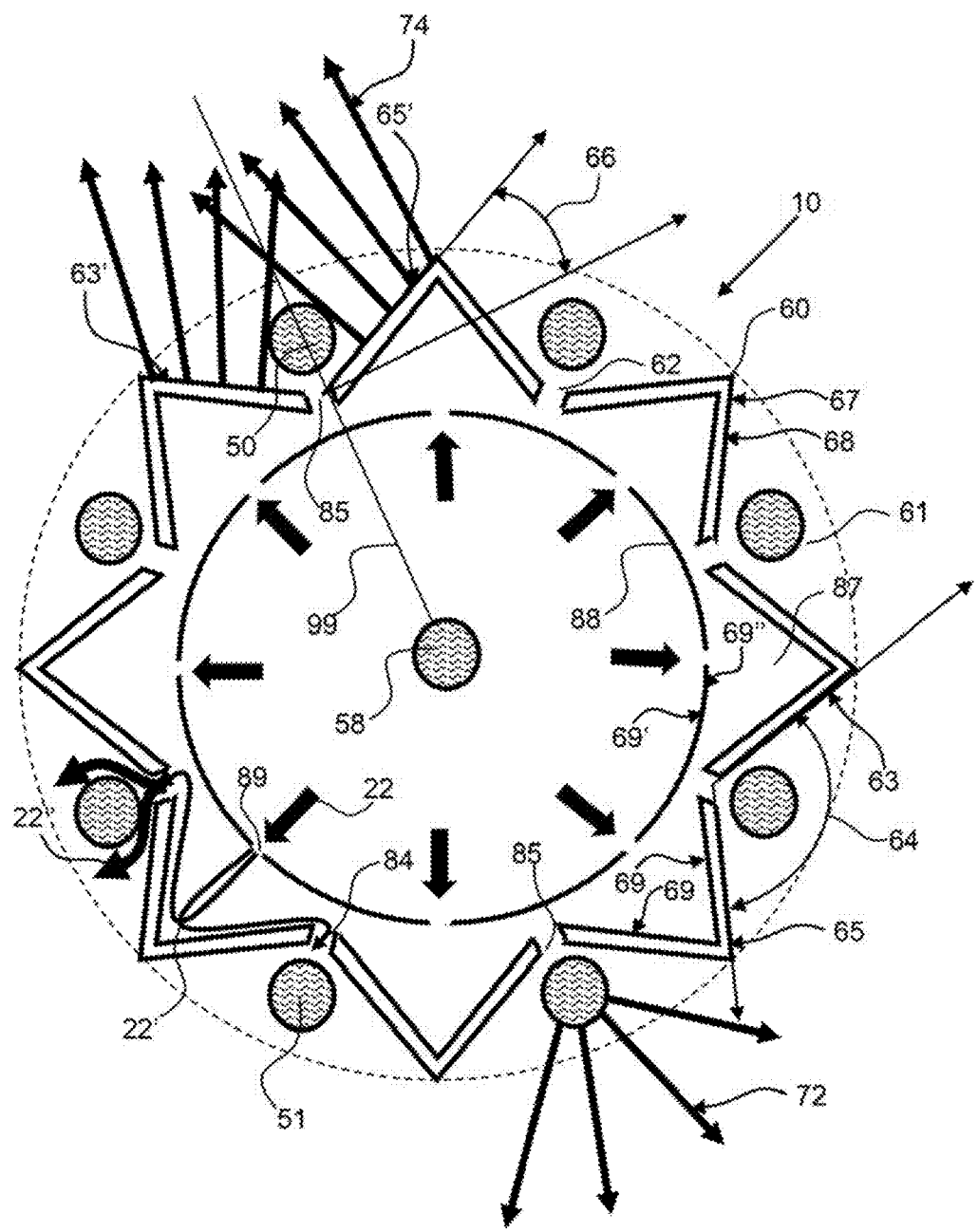
FIG. 5 shows a cross sectional view of the lamp tower taken along line 5-5 in FIG. 3, wherein the lamp tower has eight reflective cells.
Figure 6:
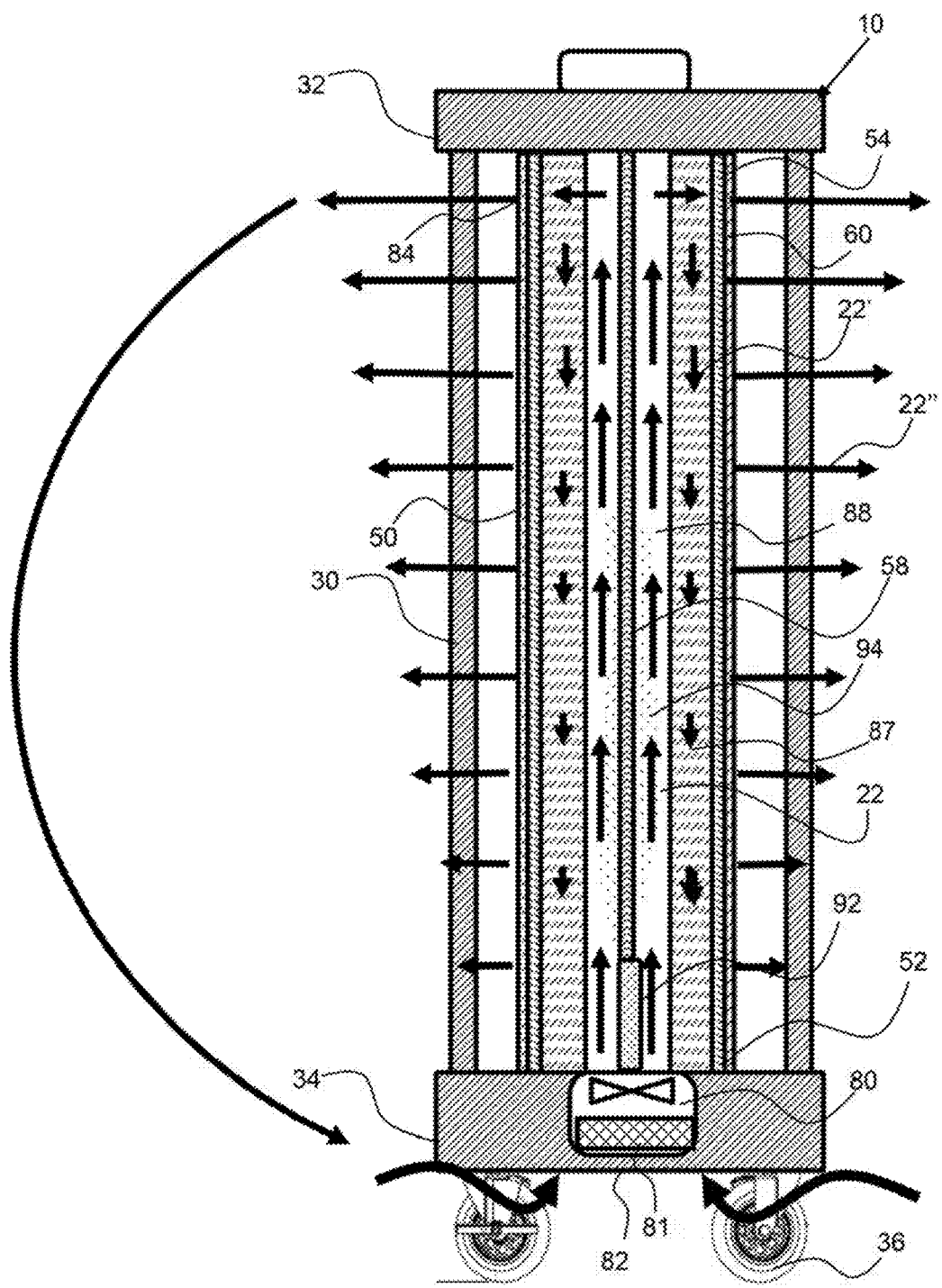
FIG. 6 shows a cross sectional view of the portable microorganism sanitation system taken along line 6-6 in FIG. 4.

Referring now to FIGS. 5 and 6, an exemplary lamp tower taken 60 comprises a first reflective light panel 63, and a second reflective panel 65 configured around the UV lamp 51. The first and second reflective light, panels are configured at offset angles to form a reflective cell 61, wherein the inclusive reflective angle 64 between the first and second reflective panels is less than 180 degrees. The reflective panels are configured at a normal offset angle 66, or angle offset from a line normal of a radial line, a line that extends radially from a center of the lamp tower 60. Put another way, the first and second reflective panels are configured at a reflective inclusive angle to each other 64, that is less than 180 degrees. The two reflective panels 63, 65 form an acute angle to a radial line 99 drawn through an intersection 62 between the two reflective panels. This configuration of reflective panels around the UV lamps produces reflected UV light 74 that is emitted at a plurality of angles. The exemplary portable microorganism sanitation system 10, therefore produces UV light 72 emitted directly from the UV light source 50, as well as reflected UV light, that is emitted at various reflected angles to provide a large range of emitted UV light angles for direct impingement on surfaces. The reflective surfaces 67 of the reflective panels, may comprises a photocatalyst 68 to treat air as it flows out from the lamp tower. The UV lamps 51 are configured along a radial line that, extends through the intersection 62 of the two reflective panels, 63, 65. The UV light sources 50 are configured within the reflective cells 61, or within a perimeter shown by the dashed circle that extends around a perimeter of the reflective panels.

Airflow 22 flows up through the lamp tower 60 from an air inlet 82 in the base and flows through an air conduit 88 configured within the air tower. The airflow 22' then flows between the air conduit 88 and the interior of the lamp tower 60 and finally out of the lamp tower through air outlets 84, such as air outlet slots 85 between the reflective panels. The airflow may be exposed to UV light as it travels up through the air conduit from the interior UV lamp 58. In addition, the interior surface of the air conduit may comprise a photocatalyst 69' to deactivate and destroy microorganisms. Finally, the interior surfaces of the lamp tower may comprise a photocatalyst 69 and the exterior surfaces of the air conduit 88 may comprise a photocatalyst 69" to destroy microorganisms in the return airflow conduit 87. The reflective panel may also comprise an exterior photocatalyst 68. As shown in FIG. 6, the airflow 22 flows through the airflow conduit 88 and then the airflow 22' flows into the space between the airflow conduit and the lamp tower 60 and finally the airflow 22" flows out of the lamp tower. This flow path of the airflow may ensure a long exposure time and therefore may more effectively destroy microorganisms. The airflow conduit may be transparent to allow the UV light from the interior lamp 58 to project through the airflow conduit and into the return airflow conduit 87, or the space between the airflow conduit and interior of the lamp tower 60. A portion of the airflow conduit may comprise a photocatalyst, such as strips or patches of photocatalyst material on the interior or external surface. The airflow may be directed to flow around the UV lamp 51 to keep the lamps cool and to provide high intensity exposure of the airflow to the UV light. An air filter 81 may be configured to filter out particles as air enters into the airflow conduit 88. An ozone generator 92 may be configured to produce ozone 94 that flows along with the airflow through the system to destroy microorganisms.

Figure 7:
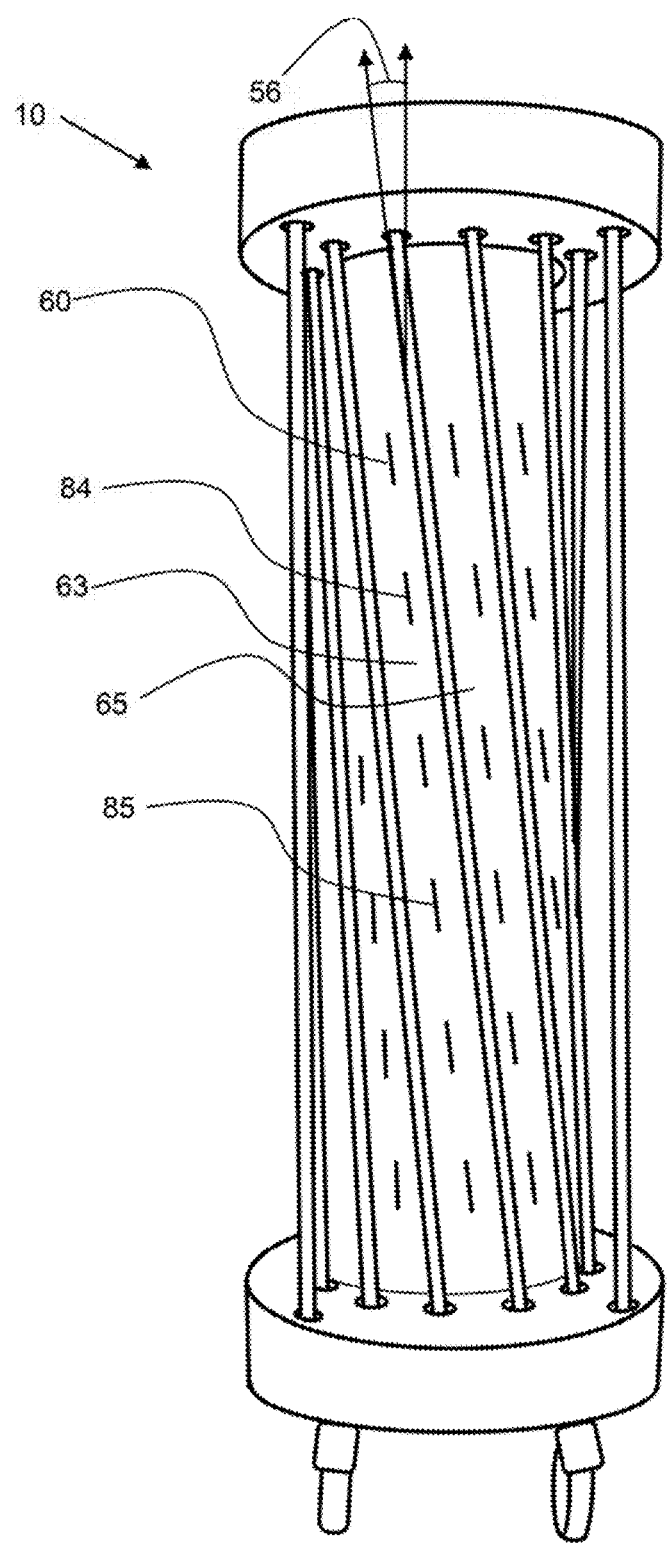
FIG. 7 shows a front view of an exemplary portable microorganism sanitation system having UV lamps and reflective panels at offset angles to vertical.

As shown in FIG. 7, an exemplary portable microorganism sanitation system 10 has UV light sources 50, such as UV lamps 51 and reflective panels 63, 65 at offset angles 56 to vertical. This may produce a better mixing of air around the unit and provides emitted UV light rays at offset angles.

Figure 8:
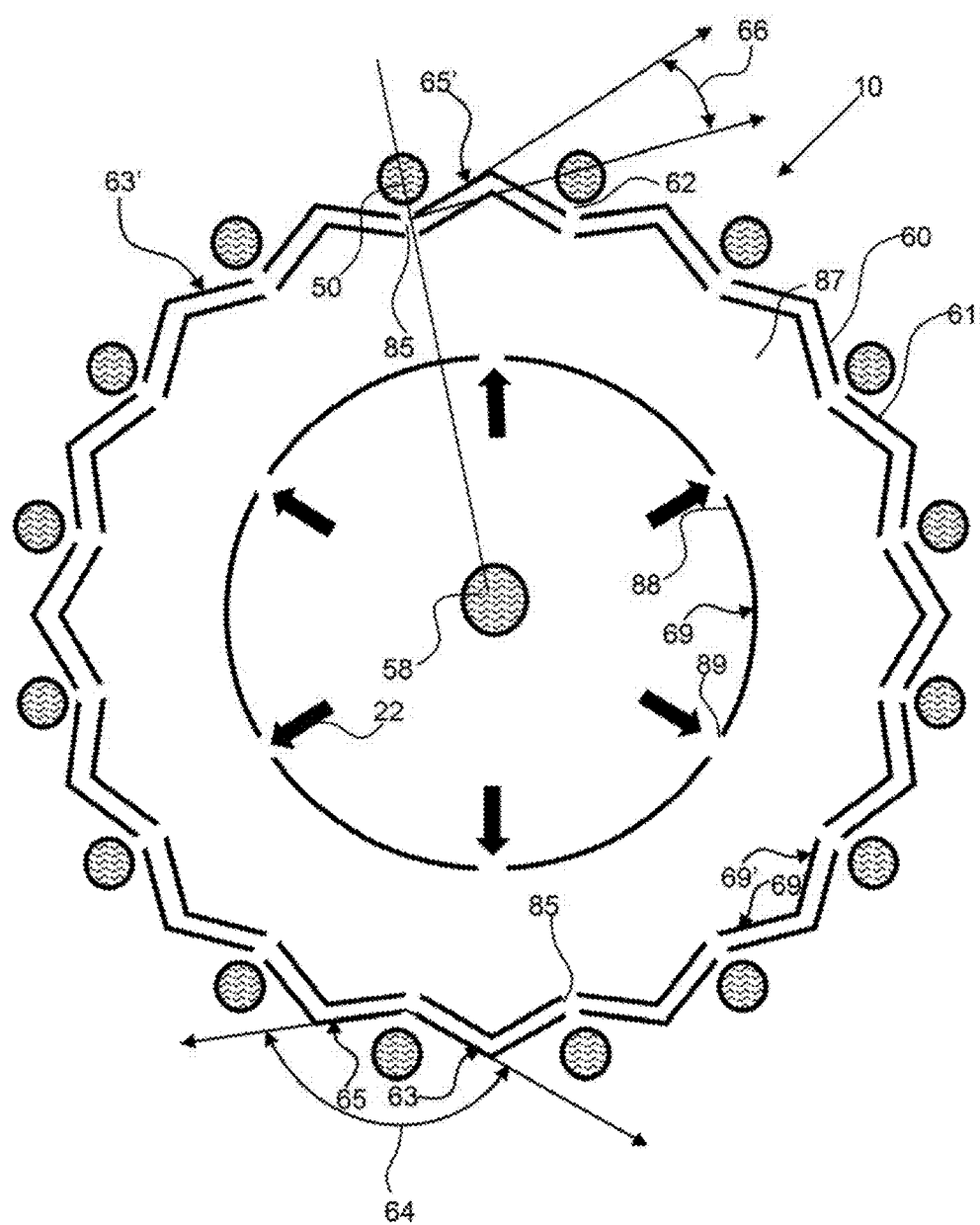
FIG. 8 shows a cross sectional view of the lamp tower taken along line 5-5 in FIG. 3.

As shown in FIG. 8 and exemplary portable microorganism sanitation system 10 has a lamp tower 60 having sixteen reflective cells 61, each having a first, reflective panel 63 and second reflective panel 65 configured at a reflective angle 64. A UV light source 50 is configured between the two reflective panels. An airflow conduit 88 is configured within the lamp tower and has a photocatalyst 69 on the interior surface. A UV light source, or interior UV lamp 58 is configured within, the airflow conduit. Ozone gas may flow up through the airflow conduit and then back down through the return airflow conduit 87. Airflow 22 flows through the interior air conduit 88 and out the air conduit outlets 89 and subsequently out of the air outlet slots 85.

FIG. 9 show a table of MERV ratings.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A portable microorganism sanitation system comprising:
   a) a lamp tower comprising:
      i) a top;
      ii) a bottom;
      iii) a perimeter; and
      iv) a plurality of reflective panels configured at offset angles to normal from the perimeter to form a plurality of reflective cells around said perimeter of the lamp tower;
   b) a plurality of UV light sources configured along the reflective cells;
   c) an airflow conduit configured within the lamp tower for receiving an airflow into said airflow conduit;
   d) an air moving device for forcing said airflow into said airflow conduit;
   e) a plurality of air outlets configured in the lamp tower; and f) one or more wheels configured on a base of the portable microorganism sanitation system;

wherein the airflow flows through the airflow conduit and out through the air outlets;

wherein UV light is emitted from the UV light sources and from the reflective panels;

wherein each air outlet is positioned between a UV light source and said airflow conduit configured within the lamp tower;

wherein the plurality of air outlets are configured along the intersection of a first reflective panel and a second reflective panel of said plurality of panels;

wherein the plurality of air outlets are slots along the intersection of the first and second reflective panels; and wherein the air outlets are discontinuous slots having different sizes from a top to a bottom of the lamp tower, whereby a different airflow is produced from the top to the bottom.

2. The portable microorganism sanitation system of claim 1, wherein the reflective panels are configured at an offset angle of between 15 degrees and 45 degrees.

3. The portable microorganism sanitation system of claim 1, wherein a first reflective panel and a second reflective panel are configured with an inclusive reflective angle of 160 degrees to 90 degrees.

4. The portable microorganism sanitation system of claim 1, comprising four or more UV light sources configured around a perimeter of the lamp tower.

5. The portable microorganism sanitation system of claim 1, wherein the UV light source is an elongated UV lamp.

6. The portable microorganism sanitation system of claim 1, wherein the UV lamp is configured within the reflective cell.

7. The portable microorganism sanitation system of claim 1, wherein the UV lamp is configured along a radial line extending through the intersection of a first and second reflective panel.

8. The portable microorganism sanitation system of claim 1, wherein at least one of the plurality of reflective panels comprises an exterior photocatalyst surface.

9. The portable microorganism sanitation system of claim 8, further comprising an interior UV light source configured within the airflow conduit.

10. The portable microorganism sanitation system of any of claim 8, wherein an interior of the lamp tower forms the airflow conduit.

11. The portable microorganism sanitation system of claim 8, wherein the airflow conduit is an internal airflow conduit configured within the interior of the lamp tower thereby forming a return airflow conduit between the internal airflow conduit and the interior of the lamp tower; wherein airflow flows through the interior airflow conduit and subsequently through the return airflow conduit before exiting through the air outlets in the lamp tower.

12. The portable microorganism sanitation system of claim 11, comprising an interior UV lamp configured in the interior of the lamp tower and wherein the internal airflow conduit is UV light translucent to allow the airflow in the interior airflow conduit and return airflow conduit to be exposed to UV light emitted by the interior UV lamp.

13. The portable microorganism sanitation system of claim 11, wherein the internal airflow conduit comprises a photocatalyst.

14. The portable microorganism sanitation system of claim 8, wherein the airflow from an airflow outlet proximal to the top of the lamp tower is greater than airflow from an airflow outlet proximal to the bottom of the lamp tower.

15. The portable microorganism sanitation system of claim 8, wherein the UV light sources extend at an offset angle to vertical of at least 10 degrees.

16. The portable microorganism sanitation system of claim 8, further comprising an air filter.

17. The portable microorganism sanitation system of claim 16, wherein the air filter filters out bacteria at a level of at least 90%.

18. The portable microorganism sanitation system of claim 16, wherein the air filter has a MERV rating of 19 or more.

19. The portable microorganism sanitation system of claim 8, further comprising an ozone generator; wherein the ozone generates ozone that flows with the airflow through the airflow conduit.

* * * * *